US008838254B2

(12) United States Patent
McClure et al.

(10) Patent No.: US 8,838,254 B2
(45) Date of Patent: Sep. 16, 2014

(54) IMPLANTABLE MEDICAL DEVICE WITH AN ELECTRONIC PRESCRIPTION

(75) Inventors: Lawrence C. McClure, Forest Lake, MN (US); Sandy K. Wixon, Andover, MN (US); Sean S. Josephson, Crystal, MN (US); Michael L. Ellingson, St. Louis Park, MN (US); Hyun J. Yoon, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 564 days.

(21) Appl. No.: 12/872,352

(22) Filed: Aug. 31, 2010

(65) Prior Publication Data

US 2011/0196447 A1 Aug. 11, 2011

Related U.S. Application Data

(60) Provisional application No. 61/303,018, filed on Feb. 10, 2010.

(51) Int. Cl.
*A61N 1/00* (2006.01)
*A61B 5/00* (2006.01)
*G06F 19/00* (2011.01)
*A61N 1/372* (2006.01)
*A61N 1/08* (2006.01)
*A61N 1/37* (2006.01)
*A61N 1/368* (2006.01)

(52) U.S. Cl.
CPC ............... *A61N 1/37* (2013.01); *A61N 1/37247* (2013.01); *A61N 2001/086* (2013.01); *A61N 1/3718* (2013.01); *A61B 5/0031* (2013.01); *G06F 19/3406* (2013.01); *A61N 1/3688* (2013.01)
USPC ............................................... 607/63; 607/59

(58) Field of Classification Search
USPC ............................................ 607/2, 59, 60, 63
See application file for complete search history.

(56) References Cited

U.S. PATENT DOCUMENTS

| 4,210,149 A | 7/1980 | Heilman et al. |
| 4,253,466 A | 3/1981 | Hartlaub et al. |
| 4,726,380 A | 2/1988 | Vollmann et al. |

(Continued)

FOREIGN PATENT DOCUMENTS

WO 2010/126935 11/2010

OTHER PUBLICATIONS (PCT/US2011/024049) PCT Notification of Transmittal of the International Search Report and the Written Opinion of the International Searching Authority, Mailed May 13, 2011, 9 pages.

(Continued)

*Primary Examiner* — Scott Getzow
(74) *Attorney, Agent, or Firm* — Michael J. Ostrom

(57) ABSTRACT

This disclosure describes techniques for configuring an IMD into the exposure operating mode. Prior to a medical procedure that generates a disruptive energy field, such as an MRI scan, an electronic prescription is configured to indicate that the IMD is authorized for the medical procedure that includes a disruptive energy field. The electronic prescription includes one or more designated bits within a storage element of the IMD. When the patient in which the IMD is implanted arrives for the medical procedure, a user (such as an MRI operator) interacts with a telemetry device to determine whether the electronic prescription is configured. Upon determining that the electronic prescription is configured, the IMD transitions into the exposure operating mode designed for operation in the disruptive energy field. In this manner, the electronic prescription confirms to the user that that the IMD has been checked for suitability for operation during the medical procedure.

29 Claims, 7 Drawing Sheets

(56) References Cited

U.S. PATENT DOCUMENTS

| | | |
|---|---|---|
| 5,836,975 A | 11/1998 | DeGroot |
| 5,987,356 A | 11/1999 | DeGroot |
| 6,311,163 B1 | 10/2001 | Sheehan et al. |
| 6,618,617 B2 | 9/2003 | Chen et al. |
| 7,082,328 B2 | 7/2006 | Funke |
| 7,212,863 B2 | 5/2007 | Strandberg |
| 7,561,915 B1 | 7/2009 | Cooke et al. |
| 2005/0070787 A1 | 3/2005 | Zeijlemaker |
| 2006/0167496 A1 | 7/2006 | Nelson et al. |
| 2007/0078497 A1 | 4/2007 | Vandanacker |
| 2007/0265685 A1 | 11/2007 | Zeijlemaker |
| 2008/0065181 A1 | 3/2008 | Stevenson |
| 2008/0242944 A1 | 10/2008 | Sharma |
| 2009/0138058 A1 | 5/2009 | Cooke et al. |
| 2010/0137945 A1 | 6/2010 | Gadagkar |

OTHER PUBLICATIONS (PCT/US2011/024043) PCT Notification of Transmittal of the International Search Report and the Written Opinion of the International Searching Authority, Mailed May 31, 2011, 11 pages.

IMPLANTABLE MEDICAL DEVICE WITH AN ELECTRONIC PRESCRIPTION

This application claims the benefit of U.S. Provisional Application No. 61/303,018, filed on Feb. 10, 2010, the content of which is incorporated herein by reference in its entirety. This application is also related to the application filed for Ser. No. 12/872,375, entitled "ELECTRONIC PRESCRIPTION ACTIVATION DEVICE" and filed on the same day as the current application.

TECHNICAL FIELD

This disclosure relates generally to implantable medical devices and, in particular, to operation of an implantable medical device when exposed to a disruptive energy field.

BACKGROUND

A wide variety of implantable medical devices (IMDs) that deliver a therapy or monitor a physiologic condition of a patient have been clinically implanted or proposed for clinical implantation in patients. IMDs may deliver therapy or monitor conditions with respect to a variety of organs, nerves, muscles or tissues of the patients, such as the heart, brain, stomach, spinal cord, pelvic floor, or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, or defibrillation via electrodes of one or more implantable leads. As another example, a neurostimulator may deliver electrical therapy signals, such as pulses, to a spinal cord, brain, pelvic floor or the like, to alleviate pain or treat symptoms of any of a number of neurological or other diseases, such as epilepsy, gastroparesis, Alzheimer's, depression, obesity, incontinence and the like.

Exposure of the IMD to a disruptive energy field may result in undesirable operation of the IMD. The IMD may be exposed to the disruptive energy field for any of a number of reasons. For example, one or more medical procedures may need to be performed on the patient within which the IMD is implanted. For example, the patient may need to have a magnetic resonance imaging (MRI) scan, computed tomography (CT) scan, electrocautery, diathermy, radio frequency (RF) ablation, lithotripsy, or other medical procedure that produces a magnetic field, electromagnetic field, electric field or other disruptive energy field.

The disruptive energy field may induce energy on one or more of the implantable leads coupled to the IMD. The IMD may inappropriately detect the induced energy on the leads as physiological signals. Alternatively, or additionally, the induced energy on the leads may result in the inability to correctly detect physiological signals. In either case, detection of the induced energy on the leads as physiological signals may result in the IMD delivering therapy when it is not desired or withholding therapy when it is desired. In other instances, the induced energy on the leads may result in stimulation or heating of the tissue and/or nerve site adjacent to the electrodes of the leads. Such heating may compromise pacing and sensing thresholds at the tissue site, which could result in reduced therapy efficacy.

SUMMARY

This disclosure describes techniques for configuring an implantable medical device (IMD) into an exposure operating mode. Prior to a medical procedure that generates a disruptive energy field, such as an MRI scan, an electronic prescription may be programmed into the IMD and an indicator is configured to indicate that the IMD is programmed with an electronic prescription. The electronic prescription may be an authorization for the medical procedure that includes a disruptive energy field as well as one or more operating parameters for use during the medical procedure.

The electronic prescription indicator includes one or more designated bits within a storage element of the IMD. When the patient in which the IMD is implanted arrives for the medical procedure, a user (such as an MRI operator) interacts with a telemetry device to determine whether the IMD is programmed with an electronic prescription. For example, the user may interrogate the IMD to determine whether the electronic prescription indicator is configured. Upon determining that the electronic prescription indicator is configured indicating that the IMD is programmed with an electronic prescription, the IMD invokes the electronic prescription. For example, the IMD may transition operation of the IMD into the exposure operating mode designed for operation in the disruptive energy field. In this manner, the electronic prescription indicator confirms to the user that the IMD has been checked for suitability for operation during the medical procedure that generates the disruptive energy field and has been authorized for the medical procedure.

In one example, this disclosure is directed to a method of configuring an implantable medical device for operation in an environment with a disruptive energy field. The method comprises configuring an electronic prescription indicator to indicate whether the implantable medical device is authorized for a medical procedure that includes the disruptive energy field, wherein the electronic prescription indicator includes one or more designated bits within a storage element of the implantable medical device. The method also includes confirming that the electronic prescription indicator of the implantable medical device is configured and invoking an exposure operating mode defined by an electronic prescription that is designed for operation in the disruptive energy field upon confirming that the electronic prescription indicator is configured.

In another example, this disclosure is directed to a medical device system comprising an implantable medical device, a first external device and a second external device. The implantable medical device includes a telemetry module to transmit and receive communications, an electronic prescription indicator that indicates whether the implantable medical device is authorized for a medical procedure that includes a disruptive energy field, wherein the electronic prescription indicator includes one or more designated bits within a storage element of the implantable medical device, an electronic prescription that defines operating parameters of an exposure operating mode that is designed for operation in the disruptive energy field, and a processor. The first external device that communicates with the implantable medical device to cause the processor to configure the electronic prescription indicator to indicate that the implantable medical device is authorized for a medical procedure that includes a disruptive energy field. The second external device that communicates with the implantable medical device to confirm that the electronic prescription indicator of the implantable medical device is configured and invoke the electronic prescription upon confirming that the electronic prescription indicator is configured.

In a further example, this disclosure is directed to an implantable medical device that includes at least one storage element, an electronic prescription indicator that includes one or more designated bits within the at least one storage element of the implantable medical device and an electronic prescription stored within the at least one storage element of the implantable medical device that defines one or more device operating parameters of an exposure operating mode for use in the disruptive energy field. The electronic prescription indicator indicates whether the implantable medical device is authorized for a medical procedure that includes a disruptive energy field. The implantable medical device also includes a transceiver that transmits and receives communications and a processor that controls operation of the implantable medical device. The processor configures the electronic prescription indicator to indicate that the implantable medical device is configured with the electronic prescription and causes the transceiver to transmit a communication that includes a value of the electronic prescription indicator in response to a communication from an external device.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
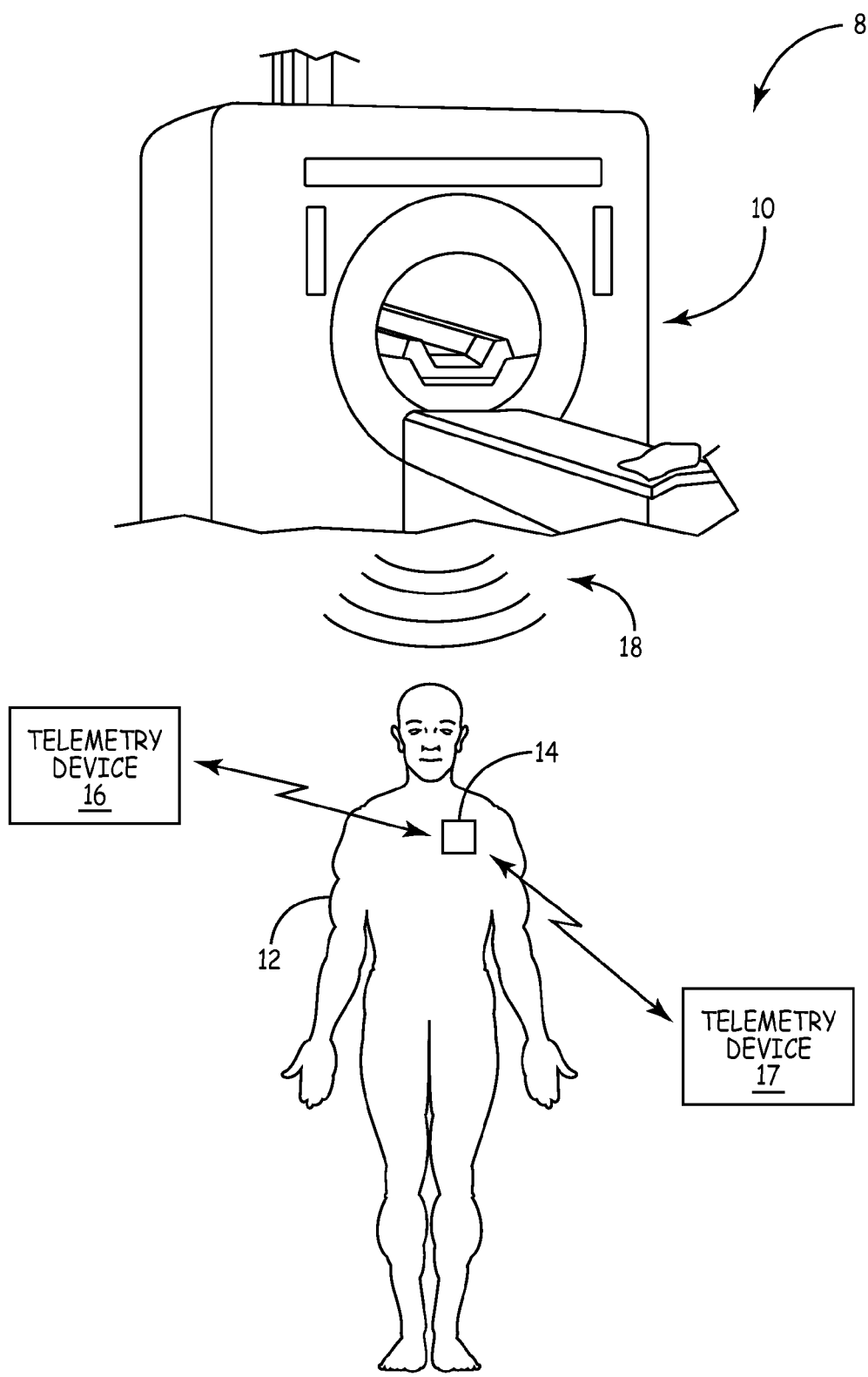
FIG. 1 is a conceptual diagram illustrating an environment in which an implantable medical device is exposed to a disruptive energy field.

FIG. 1 is a conceptual diagram illustrating a magnetic resonance imaging (MRI) device 10, a patient 12 in which an implantable medical device (IMD) 14 is implanted, and telemetry devices 16 and 17 that communicate with IMD 14 in accordance with the techniques of this disclosure. Although the techniques of this disclosure are described in the context of MRI procedures, the techniques of this disclosure may be used in conjunction with other medical or non-medical procedures that include disruptive energy fields that may interfere with operation of IMD 14.

MRI device 10 uses magnetic and radio frequency (RF) fields to produce images of body structures for diagnosing injuries and/or disorders. For example, MRI device 10 may generate a static magnetic field, gradient magnetic fields and/or RF fields. The static magnetic field is a non-varying magnetic field that is typically always present around MRI device 10 whether or not an MRI scan is in progress. Gradient magnetic fields are low-frequency pulsed magnetic fields that are typically only present while the MRI scan is in progress. RF fields are pulsed RF fields that are also typically only present while the MRI scan is in progress. The magnitude, frequency, timing or other characteristic of disruptive energy field 18 may vary based on the type of MRI scanner producing the field.

Some or all of the various types of fields produced by MRI device 10 may interfere with operation of IMD 14. In other words, one or more of the various types of fields produced by MRI device 10 may make up disruptive energy field 18. For example, the gradient magnetic fields and/or RF fields produced by MRI device 10 may induce energy on one or more implantable leads of IMD 14 or on other components (e.g., a housing) of IMD 14. The induced energy may be conducted to the tissue of patient 12 resulting in heating of the tissue adjacent to electrodes of the leads or adjacent to the housing of IMD 14. Such heating may compromise pacing and sensing thresholds at the tissue site, which could result in reduced therapy efficacy. In some instances, IMD 14 may inappropriately detect the induced energy on the leads as physiological signals, which may in turn cause IMD 14 to deliver undesired therapy or withhold desired therapy. In other instances, the induced energy on the leads may result in IMD 14 not detecting physiological signals that are actually present, which may again result in IMD 14 delivering undesired therapy or withholding desired therapy.

To reduce the undesirable effects of disruptive energy field 18, IMD 14 is capable of operating in a mode that is less susceptible to undesirable operation during exposure to disruptive energy field 18, referred to herein as the "exposure mode" or "exposure operating mode." In the case of an exposure operating mode that specifically accounts for MRI scans, the mode may be referred to as an MR Conditional mode or an MR Safe mode. Other exposure operating modes, however, may specifically account for other disruptive energy fields from different devices. IMD 14 may be configured from a normal operating mode (e.g., the current operating mode) to the exposure operating mode prior to being exposed or upon being exposed to disruptive energy field 18.

Prior to having an MRI scan or other medical procedure, IMD 14 may be analyzed to determine whether IMD 14 is suitable for operation in disruptive energy field 18. In one example, a first user, such as a cardiologist or electrophysiologist, may interact with telemetry device 17 to determine the suitability of IMD 14 for operation in disruptive energy field 18 while patient 12 undergoes a medical procedure (e.g., an MRI scan or other procedure). In another example, the first user may interact with telemetry device 17 remotely to analyze the suitability of IMD 14 for operation in disruptive energy field 18. In a further example, suitability of IMD 14 for operation in disruptive energy field 18 may be determined by looking for a radio opaque mark on IMD 14 via x-ray.

In addition to determining the suitability of IMD 14 for the MRI scan or other procedure, the first user may interact with telemetry device 17 to program an electronic prescription into IMD 14. The electronic prescription may be an authorization for the medical procedure that includes a disruptive energy field and/or one or more operating parameters for use during the MRI scan or other procedure. In some instances, the operating parameters of the exposure operating mode may be pre-stored within IMD 14 or automatically determined by IMD 14 and stored as part of the electronic prescription. In any case, upon determining that IMD 14 is suitable for operation in disruptive energy field 18 and/or programming one or more operating parameters of the exposure operating mode one or more designated bits within a storage element of IMD 14 are configured to indicate that IMD 14 is authorized for the medical procedure that includes disruptive energy field 18. The one or more designated bits that indicate that patient 12 and/or IMD 14 are authorized for the medical procedure are referred to herein as an electronic prescription indicator. In this manner, when the electronic prescription indicator is configured, it indicates that IMD 14 is programmed with an electronic prescription that authorizes patient 12 to undergo the medical procedure that subjects IMD 14 to disruptive energy field 18 and/or includes device operating parameters for use during that procedure.

At some point after programming the electronic prescription and configuring the electronic prescription indicator, patient 12 may arrive for the medical procedure, e.g., MRI scan. The MRI scan typically occurs at a different facility or a different location within the same facility with different medical personnel. The amount of time between configuring the electronic prescription and patient 12 arriving for the medical procedure may vary, and may be on the order of minutes, hours, days, or weeks. When patient 12 arrives for the medical procedure, a second user, e.g. an operator of MRI device 10, may interact with telemetry device 16 to determine whether the electronic prescription indicator is configured. When the electronic prescription indicator is configured, the second user knows that patient 12 has been authorized to undergo the medical procedure that subjects IMD 14 to disruptive energy field 18 and/or that IMD 14 may include operating parameters for device operation during the procedure. Thus, the one or more designated bits of the electronic prescription indicator may function to indicate to the operator of MRI device 10 or other personnel that IMD 14 has been checked for suitability for operating during exposure to disruptive energy field 18 and is authorized for the procedure.

Upon determining that the electronic prescription is configured, telemetry device 16 may cause IMD 14 to transition into the exposure operating mode designed for operation in disruptive energy field 18. Telemetry device 16 may, for example, transmit one or more communications that invoke the exposure operating mode. Telemetry device 16 may notify the second user that IMD 14 is now operating in accordance with the exposure operating mode. In other instances, IMD 14 may transition into the exposure operating mode automatically in response to detecting disruptive energy field 18 or other condition indicating the presence of MRI scanner 10.

The exposure operating mode is typically less susceptible to undesirable operation in disruptive energy field 18 than the normal operating mode. In other words, operating IMD 14 in the exposure mode may reduce some or all of the adverse effects caused by disruptive energy field 18. When operating in the exposure operating mode, IMD 14 is configured to operate with different functionality compared to the normal operating mode. In some instances, IMD 14 may be configured to operate with reduced functionality.

After exposure of IMD 20 to disruptive energy field 18, it is desirable to reconfigure IMD 20 back to the normal operating mode, e.g., the operating mode prior to the exposure operating mode or a default operating mode. This may be especially desirable for IMDs for which sensing or therapy is suspended during the exposure operating mode. In one example, IMD 20 may be manually reconfigured into the normal operating by a user (e.g., physician, technician or other user) interacting with one of telemetry devices 16 or 17.

In another example, IMD 20 may be automatically reconfigured to the normal operating mode, e.g., in response to expiration of a timer, in response to no longer detecting disruptive energy field 18 or other condition, or a combination of conditions.

Telemetry devices 16 and 17 may communicate with IMD 14 via wireless communication using any techniques known in the art. Examples of communication techniques may include RF telemetry, but other techniques are also contemplated. In some instances, telemetry devices 16 and 17 and IMD 14 may communicate in the 402-405 MHz frequency band in accordance with the Medical Implant Communications Service (MICS) frequency band regulation. In other instances, telemetry devices 16 and 17 and IMD 14 may communicate in the 401-402 MHz or 405-406 MHz frequency bands in accordance with the Medical External Data Service (MEDS) band regulations, in the unlicensed industrial, scientific and medical (ISM) band, or other regulated or unregulated frequency band. Additionally, telemetry devices 16 and 17 may exchange communications with IMD 14 in accordance with a communication protocol (proprietary or non-proprietary) designed for communication with IMD 14.

One or both of telemetry devices 16 and 17 may be dedicated hardware devices with dedicated software for communicating with and configuring IMD 14 as described above. Alternatively, one or both of telemetry devices 16 and 17 may be off-the-shelf computing devices (e.g., laptop, desktop, cell phone, personal digital assistant (PDA), iPod, or other computing device) running an application that enables telemetry devices 16 and 17 to communicate with and configure IMD 14 as described above. One or both of telemetry devices 16 and 17 may, in some instances, include a programming head that may be placed proximate to the patient's body near the implant site of IMD 14 in order to improve the quality or security of communication with IMD 14. One or both of telemetry devices 16 and 17 may include a user interface that receives input from the user and/or displays data to the user. Additionally, one or more of telemetry devices 16 and 17 may be coupled to a remote computing device via one or more wired or wireless networks, such as a local area network (LAN), wide area network (WAN), or global network, such as the Internet. In this manner, a user may remotely program the electronic prescription and/or remotely activate the electronic prescription remotely.

Telemetry device 16 may be designed to have very limited functionality. For example, telemetry device 16 may only be capable of interrogating IMD 14 to determine whether the electronic prescription is configured and to cause IMD 14 to enter an exposure operating mode. As such, telemetry device 16 may only be capable of reading and writing to a small number of registers in the device. The limited functionality of telemetry device 16 allows for development of a low cost telemetry device. As will be described below in more detail, telemetry device 16 may be as simple as a device with a transceiver, an antenna, a small amount of memory, and a user interface that includes one or two buttons and a light emitting diode (LED). In other instances, however, telemetry device 16 may have additional functionality. Telemetry device 16 may be kept by the facility at which a medical procedure is performed or given to a patient 12 at the time the electronic prescription is set for a patient 12 to bring along for the medical procedure.

Telemetry device 16 may be a stand-alone device. In some instances, telemetry device 16 may be MRI labeled such that it remains in the MRI suite during the MRI scan. Alternatively, telemetry device 16 may be partially located within the MRI suite. For example, an antenna of telemetry device 16 may MRI labeled such that the antenna may be located within the MRI suite while the electronic components of telemetry device 16 are located outside of the MRI suite and electrically connected to the antenna. In other instances, some or all of telemetry device 16 may be integrated within MRI device 10.

IMD 14 is implanted within patient 12 to provide therapy to or to monitor a physiological condition of patient 12. IMD 14 may be any of a variety of therapy devices. For example, IMD 14 may be a device that provides electrical stimulation therapy via one or more implantable leads that include one or more electrodes (not shown in FIG. 1). In some instances, IMD 14 may be a device that provides electrical stimulation therapy in the form of cardiac rhythm management therapy to a heart of patient 12 via leads implanted within one or more atria and/or ventricles of the heart. The cardiac rhythm management therapy delivered by IMD 14 may include pacing, cardioversion, defibrillation and/or cardiac resynchronization therapy (CRT). In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

In addition to providing electrical stimulation therapy, IMD 14 may sense one or more physiological parameters of patient 12. When one or more leads are implanted within the heart of patient 12, for example, electrodes of the leads may sense electrical signals attendant to the depolarization and repolarization of the heart to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like.

In other instances, IMD 14 may be a device that delivers a drug or therapeutic agent to patient 12 via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

Although described in the context of MRI, the techniques may be used to configure IMD 14 for exposure to sources of disruptive energy fields present during other medical or non-medical procedures, including a CT scan, electrocautery procedure, diathermy procedure, ablation procedure, radiation therapy procedure, electrical therapy procedure, magnetic therapy procedure or any other procedure with medical devices that radiate energy to produce magnetic, electromagnetic, electric fields or other disruptive energy fields.

Figure 2:
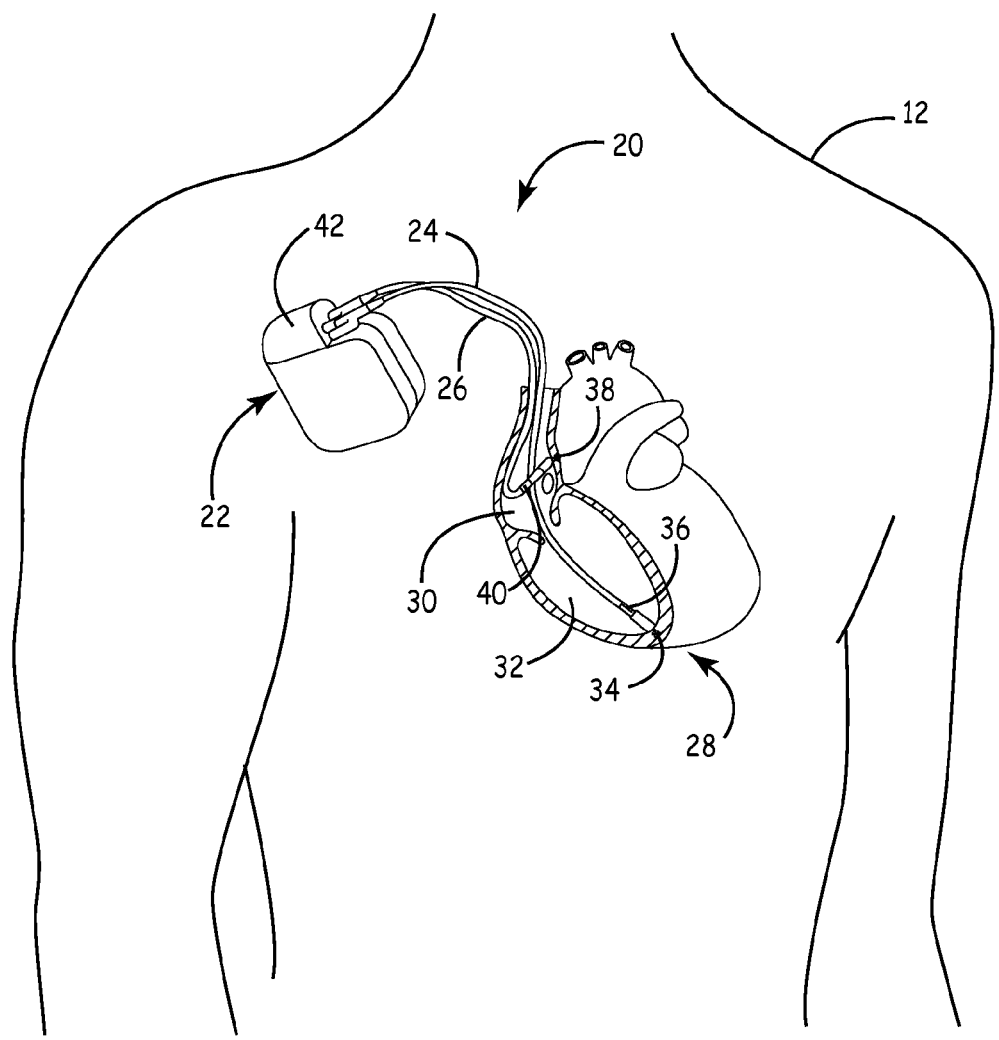
FIG. 2 is a conceptual diagram illustrating an example implantable medical device that may be used to provide therapy to patient.

FIG. 2 is a conceptual diagram illustrating an example IMD 20 that may be used to provide therapy to patient 12. IMD 20 includes a housing 22 and leads 24 and 26 that extend from housing 22. IMD 20 may, for example, correspond to IMD 14 of FIG. 1 or other IMD.

In the example illustrated in FIG. 2, IMD 20 is an implantable cardiac device that senses electrical activity of a heart 28 of patient 12 and/or provides electrical stimulation therapy to heart 28 of patient 12. The electrical stimulation therapy to heart 28, sometimes referred to as cardiac rhythm management therapy, may include pacing, cardioversion, defibrillation and/or cardiac resynchronization therapy. The combinations of cardiac therapies provided may be dependent on a condition of patient 12. In some instances, IMD 20 may provide no therapy to patient 12, but instead provide only sensing of electrical activity or other variable of heart 28, such as in the case of an implantable loop recorder.

In the illustrated example, lead 24 is a right ventricular (RV) lead that extends through one or more veins (not shown), the superior vena cava (not shown), and right atrium 30, and into right ventricle 32 of heart 28. Lead 24 includes electrodes 34 and 36 located along a distal end of lead 24. In the illustrated example, lead 26 is right atrial (RA) lead that extends through one or more veins and the superior vena cava, and into the right atrium 30 of heart 28. Lead 26 includes electrodes 38 and 40 located along a distal end of lead 26.

Electrodes 34 and 38 may take the form of extendable helix tip electrodes mounted retractably within an insulative electrode head (not shown) of respective leads 24 and 26. Electrodes 36 and 40 may take the form of ring electrodes. In other embodiments, electrodes 34, 36, 38 and 40 may be other types of electrodes. For example, electrodes 34, 36, 38 and 40 may all be ring electrodes located along the distal end of the associated lead 24 or 26. Additionally, either or both of leads 24 and 26 may include more than two electrodes or only a single electrode.

Each of the electrodes 34, 36, 38 and 40 may be electrically coupled to a respective conductor within the body of its associated lead 24 and 26. The respective conductors may extend from the distal end of the lead to the proximal end of the lead and couple to circuitry of IMD 20. For example, leads 24 and 26 may be electrically coupled to a stimulation module, a sensing module, or other modules of IMD 20 via connector block 42 of housing 22. In some examples, proximal ends of leads 24 and 26 may include electrical contacts that electrically couple to respective electrical contacts within connector block 42. In addition, in some examples, leads 24 and 26 may be mechanically coupled to connector block 42 with the aid of set screws, connection pins or another suitable mechanical coupling mechanism.

When IMD 20 is capable of delivering electrical stimulation therapy, IMD 20 delivers the therapy (e.g., pacing pulses) to heart 28 via any combination of electrodes 34, 36, 38 and 40 to cause depolarization of cardiac tissue of heart 28. For example, IMD 20 may deliver bipolar pacing pulses to right atrium 30 via electrodes 38 and 40 of lead 26 and/or may deliver bipolar pacing pulses to right ventricle 32 via electrodes 34 and 36 of lead 24. In another example, IMD 20 may deliver unipolar pacing pulses to atrium 30 and ventricle 32 using housing 22 as an electrode in conjunction with one of electrodes 34, 36, 38 and 40. The housing electrode may be formed integrally with an outer surface of the hermetically-sealed housing of IMD 20 or otherwise coupled to housing 22. In some examples, the housing electrode is defined by an uninsulated portion of an outward facing portion of housing 22 of IMD 20.

Electrodes 34, 36, 38 and 40 may also sense electrical signals attendant to the depolarization and repolarization of heart 28. The electrical signals are conducted to IMD 20 via one or more conductors of respective leads 24 and 26. IMD 20 may use any combinations of the electrodes 34, 36, 38, 40 or the housing electrode for unipolar or bipolar sensing. As such, the configurations of electrodes used by IMD 20 for sensing and pacing may be unipolar or bipolar depending on the application. IMD 20 may analyze the sensed signals to monitor a rhythm of heart 28 or detect an arrhythmia of heart 28, e.g., tachycardia, bradycardia, fibrillation or the like. In some instances, IMD 20 provides pacing pulses (or other therapy)

to heart 28 based on the cardiac signals sensed within heart 28. In other words, pacing may be responsive to the sensed events.

As described above, exposure of IMD 20 to a disruptive energy field 18 may result in undesirable operation. For example, gradient magnetic or RF fields produced by MRI device 10 may induce energy on one or more conductors of respective ones of implantable leads 24 and 26 or on the housing electrode. In some instances, the induced energy on conductors of leads 24 or 26 or on components of IMD 20 results in heating of the tissue adjacent to electrodes 34, 36, 38 and 40 or housing 22 of IMD 20. Such heating may compromise pacing and sensing thresholds at the tissue, which could result in reduced therapy efficacy. In other instances, IMD 20 may inappropriately detect the induced energy on the conductors of leads 24 or 26 as physiological signals, which may in turn cause IMD 20 to deliver undesired therapy or withhold desired therapy. In further instances, the induced energy on the conductors of leads 24 or 26 may result in IMD 20 not detecting physiological signals that are actually present, which may again result in IMD 20 delivering undesired therapy or withholding desired therapy.

Configuring IMD 20 into an exposure operating mode may reduce the undesirable effects that may be caused by exposure to disruptive energy field 18. As such, IMD 20 may be configured to operate in the exposure operating mode using the electronic prescription techniques described in this disclosure. The exposure operating mode is typically less susceptible to undesirable operation in disruptive energy field 18 than the normal operating mode. In other words, operating IMD 20 in the exposure mode may reduce some or all of the adverse effects caused by disruptive energy field 18. When operating in the exposure operating mode, IMD 20 is configured to operate with different functionality compared to the normal operating mode. In some instances, IMD 20 may be configured to operate with reduced functionality. In other instances, IMD 20 may be configured to the same or increased functionality.

For example, IMD 20 may operate in an exposure operating mode in which sensed signals (e.g., those caused by energy induced on the leads) do not affect delivery of therapy. If patient 12 is pacing dependent, for example, the exposure mode of IMD 20 may correspond to an asynchronous pacing mode with no sensing, e.g., AOO, VOO or DOO. In another example, the exposure mode of IMD 20 may correspond to an asynchronous pacing mode that includes sensing, but has no mode of response to the pacing, e.g., such as a AAO, AVO, ADO, VVO, VAO, VDO, DDO, DAO or DVO pacing mode. In either of these cases, pacing is provided with no modification due to sensing. As such, the induced energy on the leads caused by disruptive energy field 18 does not result in undesirable operation of IMD 20.

In another example, the exposure operating mode of IMD 20 may correspond to a sensing only mode, such as OAO, OVO or ODO, in which no pacing is provided. Such modes may only be used in cases in which patient 12 is not pacing dependent. Because there is no pacing in these pacing modes, such pacing modes may prevent IMD 20 from delivering undesirable stimulation or withholding desirable stimulation due to the induced energy on the leads.

The exposure mode may also suspend temporary operation of other functionality of IMD 20, particularly those that may function incorrectly when exposed to disruptive energy field 18. Some example functionality that may be suspended while operating in the exposure mode include tachycardia detection and therapy, fibrillation detection and therapy, impedance measurements, battery measurements, P- and R-wave measurements. Additional functionality that may be suspended while in the exposure mode includes collection of diagnostic data.

In other instances, IMD 20 may be operating with approximately the same functionality or even increased functionality in the exposure mode. For example, IMD 20 may use a different sensor or algorithm to detect cardiac activity of the heart of patient 12 during the exposure operating mode, such as pressure sensor measurements rather than electrical activity of the heart as used in the normal operating mode. As another example, IMD 20 may implement one or more filters that filter out the undesirable signals during the exposure operating mode that may not be implemented in the normal operating mode. In a further example, IMD 20 may implement one or more shunts or traps during the exposure operating mode to redirect the energy away from the tissue adjacent to the electrodes.

IMD 20 illustrated in FIG. 2 is merely an example of a type of IMD within which the techniques of this disclosure may be used. In other examples, IMD 20 may include more or fewer leads. For example, IMD 20 may include three leads, e.g., a third lead implanted within a left ventricle of heart 28. In another example, IMD 20 may include only a single lead that is implanted within either an atrium or ventricle of heart 28. As such, IMD 20 may be used for single chamber or multi-chamber cardiac rhythm management therapy.

In addition to more or fewer leads, each of the leads may include more or fewer electrodes. In instances in which IMD 20 is used for therapy other than pacing, e.g., defibrillation or cardioversion, the leads may include elongated electrodes, which may, in some instances, take the form of a coil. IMD 20 may deliver defibrillation or cardioversion shocks to heart 28 via any combination of the elongated electrodes and housing electrode. As another example, IMD 20 may include leads with a plurality of ring electrodes, e.g., as used in some implantable neurostimulators.

In still other examples, a medical system may include epicardial leads and/or patch electrodes instead of or in addition to the transvenous leads 24 and 26 illustrated in FIG. 2. Further, IMD 20 need not be implanted within patient 12. In examples in which IMD 20 is not implanted in patient 12, IMD 20 may deliver electrical stimulation therapy to heart 28 via percutaneous leads that extend through the skin of patient 12 to a variety of positions within or outside of heart 28.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
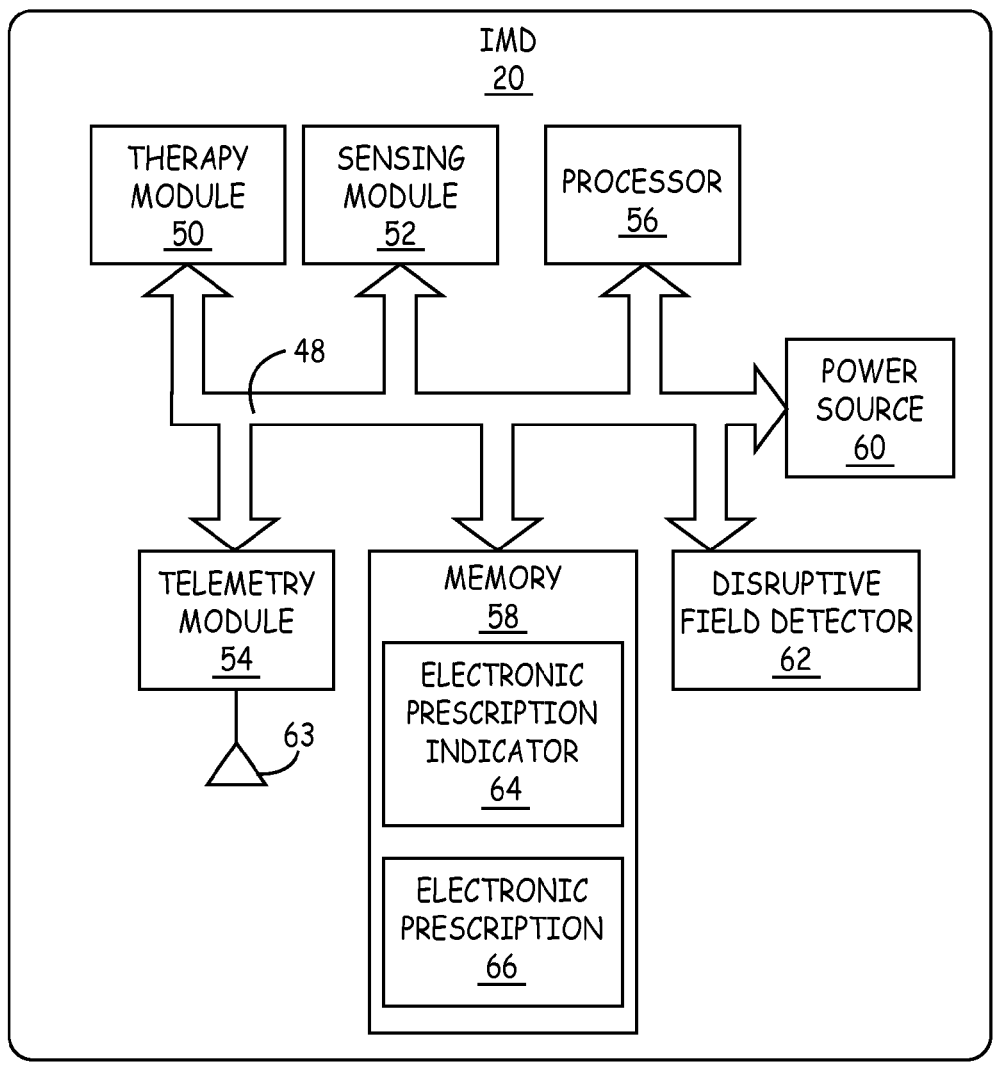
FIG. 3 is a functional block diagram of an example configuration of components of the implantable medical device of FIG. 2.

FIG. 3 is a block diagram illustrating IMD 20 in further detail. IMD 20 includes a therapy module 50, sensing module 52, telemetry module 54, processor 56, memory 58, power source 60, and disruptive field detector 62. The components of IMD 20 may be interconnected by data bus 48, by one or more direct electrical or non-electrical connections, or a combination thereof. In accordance with the techniques of this disclosure, IMD 20 further includes an electronic prescription indicator 64. Electronic prescription indicator 64 includes one or more designated bits that may be configured to indicate that IMD 20 is programmed with an electronic prescription 66 authorizing IMD 20 for a medical procedure that includes disruptive energy field 18 and/or providing device operating parameters for use during that procedure. Electronic prescription indicator 64 may also indicate the type of medical procedure for which IMD 20 has been authorized. In the example illustrated in FIG. 3, electronic prescription indicator 64 is located within memory 58. In other examples, however, electronic prescription indicator 64 may be located within a different storage element of IMD 20, such as within a register or other internal memory of processor 56.

Prior to having a medical procedure for which patient 12 has been indicated, such as an MRI scan, it is determined whether IMD 20 is suitable for operation in disruptive energy field 18. In one example, a person may determine whether IMD 20 is MRI labeled by looking for a radio opaque mark on IMD 20 in an x-ray of a chest of patient 12. In another example, a user may interact with a telemetry device (e.g., telemetry device 17) to determine a product serial number, model number, model type or other identifier of IMD 20 and use the identifier to determine whether IMD 20 is MRI labeled. The identifier may be a designated bit in a memory, on an RFID tag or other storage element of IMD 20. In a further example, the user may interact with telemetry device 17 to cause IMD 20 to perform one or more tests, including lead impedance measurements, pacing threshold measurements, sensing threshold measurements, or battery measurements, to determine whether IMD 20 is suitable for operation in disruptive energy field 18. The user may make the determination as to suitability in a clinical setting or remotely via one or more networks.

IMD 20 is programmed with electronic prescription 66. IMD 20 may receive one or more communications to program one or more device operating parameters of the exposure operating mode, i.e., for use during the authorized medical procedure. For example, a user may specify a pacing mode (e.g., atrial-based pacing mode, ventricular-based pacing mode or dual-chamber based pacing mode), pacing amplitude, pacing pulse width, and/or pacing rate of the therapy energy delivered during the exposure operating mode. As another example, the user may specify filtering configurations to be used during the exposure operating mode. In this manner, the user may program electronic prescription 66 within IMD 20 to define the operating parameters to be used during the medical procedure. In instances in which no device operating parameters need to be changed during exposure to disruptive energy field 18, electronic prescription 66 may be programmed only with the authorization for the medical procedure.

Alternatively, processor 56 may automatically determine at least a portion, and in some cases all, of the operating parameters of the exposure operating mode. One example technique for automatically determining one or more parameters of the exposure operating mode is described in copending patent application Ser. No. 12/569,101 to Ellingson et al., entitled, "AUTOMATIC SELECTION OF PARAMETERS OF AN EXPOSURE MODE OF AN IMPLANTABLE MEDICAL DEVICE," which was filed on Sep. 29, 2009 and which is incorporated herein by reference in its entirety. In this manner, IMD 20 may generate electronic prescription 66 or modify electronic prescription 66 provided by the user. Processor 56 stores the operating parameters received from telemetry device 17 or generated by processor 56 within memory 58 for later retrieval. In another example, the operating parameters of the exposure operating mode may be pre-programmed into memory 58.

Upon determining that IMD 20 is suitable for operation in disruptive energy field 18 and, in some instances, programming electronic prescription 66, IMD 20 configures electronic prescription indicator 64. Processor 56 may automatically configure electronic prescription indicator 64 when electronic prescription 66 programmed. Alternatively, IMD 20 may receive one or more communications via telemetry module 54 and antenna 63 to configure electronic prescription indicator 64 to indicate that IMD 20 is authorized for the MRI scan or other medical procedure that includes disruptive energy field 18. When electronic prescription indicator 64 is a single designated bit, processor 56 may set or assert the designated bit in response to the communication from telemetry device 17. In this case, electronic prescription indicator 64 indicates that IMD 20 is authorized for the MRI scan when the designated bit is set or asserted and indicates that IMD 20 is not authorized for the MRI scan when designated bit is not set or asserted. When electronic prescription indicator 64 includes a plurality of designated bit, processor 56 sets or configures the plurality of designated bits in response to the communication from telemetry device 17. In this case, electronic prescription indicator 64 may not only be configured to indicate that IMD 20 is authorized for a medical procedure, but electronic prescription indicator 64 may also be used to indicate which type of medical procedure IMD 20 is authorized for. For example, electronic prescription indicator 64 may be set to a first code to indicate authorization for a first medical procedure, e.g., an MRI scan, and be set to a second code to indicate authorization for a second medical procedure, e.g., an ablation procedure.

As described above, the operating parameters of the exposure operating mode may be pre-programmed into memory 58 and selected by a user based on electronic prescription indicator 64. For example, memory 58 may include an electronic prescription for exposure to an MRI device and an electronic prescription for exposure to a radio frequency ablation device. Processor 56 determines electronic prescription 66 to be used is the MRI exposure mode when electronic prescription indicator 64 is set to the first code corresponding with the MRI scan and processor 56 determines electronic prescription 66 to be used an ablation exposure mode when electronic prescription indicator 64 is set to the second code corresponding with the ablation procedure.

At some point after electronic prescription indicator 64 is configured via the first telemetry device (e.g., telemetry device 17 of FIG. 1), patient 12 arrives for the medical procedure, e.g., MRI scan. The amount of time between when electronic prescription 66 is configured and when patient 12 arrives for the medical procedure may vary, and may be as short as minutes and as long as weeks. As such, it may be desirable that processor 56 of IMD 20 update the electronic prescription (e.g., the operating parameters of the exposure operating mode) between when electronic prescription 66 is configured and when patient 12 arrives for the medical procedure. For example, processor 56 may update one or more operating parameters of the exposure operating mode based on implant history and/or system performance, such as whether or not therapy has been provided, pacing modes in which the device operated, amplitudes of the therapy energy delivered, pulse widths of the therapy energy delivered, heart rate during a predetermined period of time, or the like. In this manner, processor 56 may continuously update electronic prescription 66. In another example, processor 56 may update electronic prescription indicator 64 based on detection of a lead related condition, e.g., lead fracture or other failure. In particular, in response to detecting a lead related condition, processor 56 may clear electronic prescription indicator, e.g., reset, deassert or reconfigure electronic prescription indicator 64 to the default value indicating that IMD 20 is not authorized for the medical procedure.

In some instances, electronic prescription indicator 64 has an expiration. In this case, processor 56 may initiate a timer (not shown in FIG. 3) to track the amount of time that has elapsed since electronic prescription indicator 64 is configured. Processor 56 may clear electronic prescription indicator 64 (e.g., reset, deassert or reconfigure electronic prescription indicator 64 default value) upon expiration of the timer. In the case of a count down timer, the timer expires upon reaching zero. In the case of a count up timer, the timer may be expires upon reaching a threshold value.

When patient 12 arrives for the medical procedure, a second user, e.g. an operator of MRI device 10, may interact with telemetry device 16 to determine whether electronic prescription indicator 64 has been configured. IMD 20 receives a telemetry communication to interrogate IMD 20 regarding electronic prescription indicator 64. In response to the communication, IMD 20 transmits a communication to telemetry device 16 with the value of electronic prescription indicator 64 or an indication as to whether electronic prescription indicator 64 has been configured.

After transmitting the communication to telemetry device 16 indicating that electronic prescription indicator 64 has been configured, processor 56 may invoke electronic prescription 66. In particular, processor 56 transitions IMD 20 into the exposure operating mode designed for operation in disruptive energy field 18. IMD 20 may receive a second command from telemetry device 16 and processor 56 may transition IMD 20 into the exposure operating mode in response to the second communication. In this manner, telemetry device 16 invokes the exposure operating mode defined by electronic prescription 66. The second communication from telemetry device 16 may, for example, assert, set, or otherwise configure an operating mode register of IMD 20 that enables IMD 20 to enter the exposure operating mode. In another example, processor 56 may transition IMD 20 into the exposure operating mode automatically in response to receiving the interrogation command from telemetry device 16.

Upon entering the exposure operating mode, IMD 20 may also transmit a communication to telemetry device 16 to indicate that IMD 20 is now operating in accordance with the exposure operating mode defined by electronic prescription 66. In this manner, confirmation that IMD 20 is operating in the exposure operating mode may be obtained before performing the MRI scan or other medical procedure.

If electronic prescription indicator 64 is not configured or IMD 20 is not interrogated prior to exposure to disruptive energy field 18, IMD 20 may still enter an exposure operating mode upon exposure to disruptive energy field 18. For example, processor 56 may configure IMD 20 into a default exposure operating mode (when electronic prescription indicator 64 is not configured) or into the configured exposure operating mode defined by electronic prescription 66 (when electronic prescription indicator 64 is configured) in response to disruptive field detector 62 detecting the existence of an environment have a potentially disruptive energy field, such as in response to detecting a large static magnetic field associated with an MRI device. In this manner, even when an electronic prescription is not programmed, IMD 20 operates in accordance with parameters that reduce the likelihood of interference from disruptive energy field 18.

After exposure of IMD 20 to disruptive energy field 18 or upon occurrence of a serious medical event, processor 56 reconfigures IMD 20 back to the normal operating mode, e.g., the operating mode prior to the exposure operating mode or some other default operating mode. In one example, processor 56 may receive a telemetry communication from telemetry device 16 that causes processor 56 to reconfigure IMD 20 back to normal operating mode. Processor 56 may, for instance, deassert, reset or otherwise reconfigure the operating mode register and/or electronic prescription indicator 64 in response to the telemetry communication. In this manner, IMD 20 is manually reconfigured into the normal operating by a user (e.g., physician, technician or other user) interacting with telemetry device 16. IMD 20 may be reconfigured into the normal operating mode by user interacting with telemetry device 17 in a similar manner.

In another example, processor 56 of IMD 20 may automatically reconfigure IMD 20 to the normal operating mode, e.g., in response to expiration of a timer, in response to disruptive field detector 62 no longer detecting disruptive energy field 18 or other condition, or a combination of conditions. In this case, processor 56 deasserts, resets or otherwise reconfigures the operating mode register and/or electronic prescription indicator 64 in response to the condition or conditions. Disruptive field detector 62 may include one or more sensors that detect disruptive energy field 18, such as a Hall sensor, a reed switch, or other magnetic field detector. In some instances, disruptive field detector 62 may be within housing 22 of IMD 20. For example, disruptive field detector 62 may be the same field detector used to sense a magnetic programming head of a programming device. Alternatively, IMD 20 may be coupled to a disruptive field detector 62 located outside of housing 22 of IMD 20. Whether reconfigured into the normal operating mode automatically or manually, processor 56 may transmit telemetry communication to confirm that processor 56 is now operating IMD 20 in the normal operating mode.

Telemetry module 54 of IMD 20 communicates wirelessly with telemetry devices 16 and 17 by any of a number of wireless communication techniques. Example wireless communication techniques include RF telemetry, but other techniques are also contemplated. To this end, telemetry module 54 may include any suitable hardware, firmware, software or any combination thereof for wireless communication. For example, telemetry module 54 may include appropriate modulation, demodulation, frequency conversion, filtering, and amplifier components for transmission and/or reception of data.

Telemetry module 54 of IMD 20 also communicates in accordance with one or more communication protocols designed for communication with IMD 20. The telemetry signal transmitted by telemetry module 54 may conform to the specifications of a proprietary communication protocol. In other instances, the telemetry signal may conform to the specifications of a non-proprietary communication protocol, such as a protocol assigned by a standards organization (e.g., Institute of Electrical and Electronics Engineers (IEEE), International Organization for Standardization (ISO), International Telecommunication Union—Telecommunication Standardization Sector (ITU-T), International Telecommunication Union—Radiocommunication Sector (ITU-R), or Internet Engineering Task Force (IETF)).

In general, the communication protocol is a set of standards for communicating data between devices over a communication channel. The communication protocol may, for example, define standards for data representation, signaling, authentication, error detection or the like. The communication protocol may be broken down into layers that define characteristics for the distinct communication layers. In one example, the layers may be modeled on one or more of the layers defined by the International Open System Interconnect (OSI) reference model, although the layers may be adapted as needed.

The OSI reference model defines a physical layer, a data link layer, a network layer, a transport layer, a session layer, a presentation layer and an application layer.

IMD 20 of FIG. 3 includes a therapy module 50 and a sensing module 52. As such, IMD 20 illustrated in FIG. 3 may provide both sensing and therapy functionality. Although FIG. 3 includes both therapy module 50 and sensing module 52, IMD 20 may only provide sensing functionality and no therapy as in the case of an implantable loop recorder. In such cases, IMD 20 may not include therapy module 50. Alternatively, IMD 20 may provide therapy with no sensing. In such cases, IMD 20 may not include sensing module 52.

Sensing module 52 is configured to monitor one or more physiological signals using one or more sensors connected to sensing module 52. In one example, sensing module 52 is configured to monitor signals sensed by one or more of electrodes 34, 36, 38, and 40 on leads 24 and 26 extending from IMD 20. In another example, sensing module 52 may be configured to monitor signals sensed by a sensor within or on IMD 20, such as disruptive field detector 62. In a further example, sensing module 52 may be configured to receive signals sensed by one or more wireless or lead-less sensors and transmitted wirelessly to IMD 20. The one or more sensors may sense physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels or other parameter.

Sensing module 52 may store the sensed signals in memory 58. In some instances, sensing module 52 may store the sensed signals in raw form. In other instances, sensing module 52 may process the sensed signals and store the processed signals in memory 58. For example, sensing module 52 may include one or more amplifiers and/or filters to amplify and filter the sensed signal and store the filtered signal in memory 58. The signals stored by sensing module 52 may, in some cases, be retrieved and further processed by processor 56. In some instances, processor 56 may control the timing, amplitude, or other aspect of the therapy delivered to patient 12 based on the one or more sensed signals.

IMD 20 may also provide therapy, such as electrical stimulation therapy or drug delivery therapy, to patient 12 in accordance with parameters of one or more selected therapy programs. In particular, processor 56 controls therapy module 50 to deliver therapy to patient 12 according to one or more therapy programs, which may be received from telemetry device 17 and stored in memory 58. In the case of electrical stimulation therapy, therapy module 50 may include a stimulation generator that generates and delivers electrical stimulation therapy, e.g., in the form of pulses or shocks. Processor 56 may control the stimulation generator to deliver electrical stimulation pulses with amplitudes, pulse widths, frequency, and/or electrode polarities specified by the one or more therapy programs. In the case of drug delivery therapy, therapy module 50 may include a pump that delivers a drug or therapeutic agent to patient 12. Processor 56 may control the pump to deliver the drug or therapeutic agent with the dosage and frequency (or rate) specified by the one or more therapy programs.

Power source 60 of IMD 20 delivers operating power to the components of telemetry device 16. Power source 60 may include a rechargeable or non-rechargeable battery, or other power source. A non-rechargeable battery may be selected to last for several years, while a rechargeable battery may be charged from an external charging device on a daily or weekly basis.

Processor 56 may control operation of IMD 20, e.g., by controlling operation of the various components of IMD 20. Memory 58 may include computer-readable instructions that, when executed by processor 56, cause IMD 20 to perform various functions attributed to the components of IMD 20 herein. Memory 58 may also store sensed data and operating parameters received via telemetry from telemetry device 17.

Processor 56 may include one or more of a microprocessor, a controller, a DSP, an ASIC, an FPGA, or equivalent discrete or integrated logic circuitry. In some examples, processor 56 may include multiple components, such as any combination of one or more microprocessors, one or more controllers, one or more DSPs, one or more ASICs, or one or more FPGAs, as well as other discrete or integrated logic circuitry. The functions attributed to processor 56 herein may be embodied as software, firmware, hardware or any combination thereof. Memory 58 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media or a combination thereof.

IMD 20 is illustrated for exemplary purposes. IMD 20 may include more or fewer components than shown in FIG. 3 depending on the application of the devices. As such, the techniques described in this disclosure should not be limited by the example IMD 20 illustrated in FIG. 3.

Figure 4:
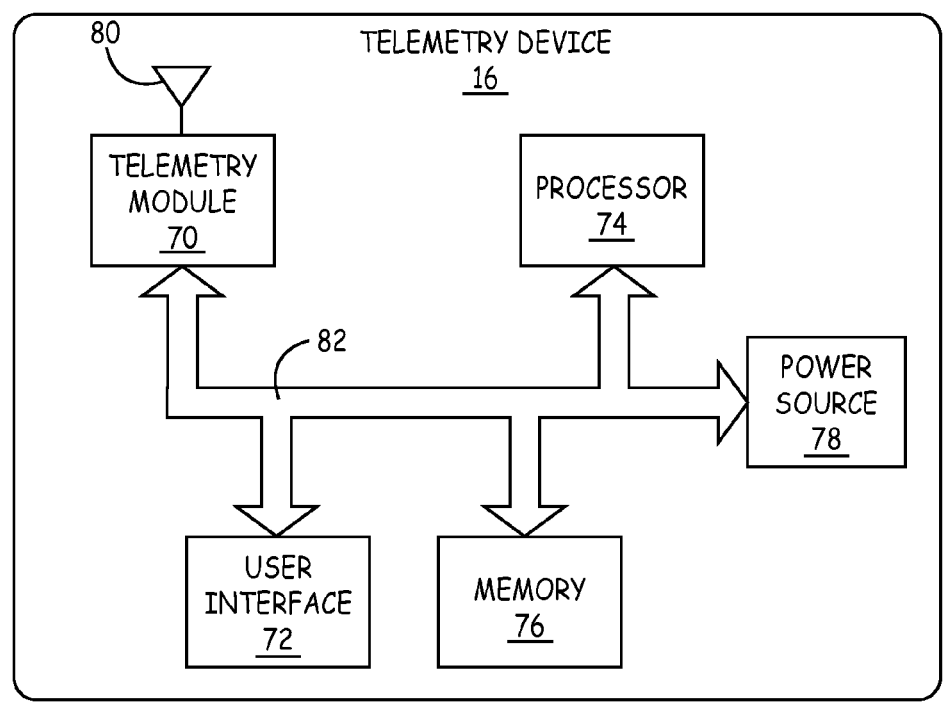
FIG. 4 is a block diagram illustrating an example configuration of components of a telemetry device used to invoke an exposure operating mode of an IMD upon confirming that an electronic prescription is set in the IMD.

FIG. 4 is a block diagram illustrating an example telemetry device 16 that invokes an exposure operating mode of IMD 20 upon confirming that electronic prescription indicator 64 is set. Telemetry device 16 includes a telemetry module 70, user interface 72, processor 74, memory 76, and power source 78, which may be interconnected via a data bus 82, direct electrical or non-electrical connections or a combination thereof.

As described above, IMD 20 may be analyzed to determine whether IMD 20 is suitable for operation in disruptive energy field 18 and, if so, electronic prescription 66 is programmed and electronic prescription indicator 64 of IMD 20 is configured. When patient 12 arrives for the medical procedure, a user, such as an operator of MRI device 10, interacts with user interface 72 of telemetry device 16 to interrogate IMD 20 to determine whether electronic prescription indicator 64 of IMD 20 has been configured. In particular, the second user may interact with an input mechanism of user interface 72 of telemetry device 16 to cause telemetry device 16 to send one or more telemetry communications via telemetry module 70 and antenna 80 to interrogate IMD 20 regarding electronic prescription indicator 64. In one example, user interface 72 may include an interrogation button that the user actuates to initiate interrogation of IMD 20. In response to actuation of the interrogation button, processor 74 may generate a telemetry communication in accordance with the communication protocol and control telemetry module 70 to transmit the telemetry communication to IMD 20 to determine whether electronic prescription indicator 64 is configured. User interface 72 may include other input mechanisms, such as more buttons, a keypad, a peripheral pointing device, a touch screen, microphone or the like.

Telemetry device 16 may receive a telemetry communication from IMD 20 via telemetry module 70 and antenna 80 indicating whether electronic prescription 66 of IMD 20 is configured. The telemetry communication from IMD 20 may indicate a value of electronic prescription indicator 64 and processor 74 of telemetry device 16 may determine whether electronic prescription 66 is programmed based on the indicated value of electronic prescription indicator 64. In the example in which electronic prescription indicator 64 is one designated bit, processor 74 may determine that electronic prescription 66 is configured when equal to "1" and determined that electronic prescription 66 is not configured when equal to "0." As such, when electronic prescription indicator 64 is set equal to "1" telemetry device 16 determines that IMD 20 is authorized for the MRI scan and when electronic prescription indicator 64 is set equal to "0" telemetry device 16 determines that IMD 20 is not authorized for the MRI scan.

In other instances, electronic prescription indicator 64 may be more than one designated bit and memory 76 of telemetry device 16 may maintain a mapping that maps values of electronic prescription indicator 64 to corresponding medical procedures. Electronic prescription indicator 64 may, for example, correspond with two designated bits such that the electronic prescription indicator 64 may take on four different values with "00" corresponding with no electronic prescription, "01" corresponding with an electronic prescription for a first medical procedure, "10" corresponding with an electronic prescription for a second medical procedure, and "11" corresponding with an electronic prescription for a third medical procedure. In this manner, electronic prescription indicator 64 is not only used to indicate IMD 20 is authorized for a medical procedure, but also indicates the type of medical procedure for which IMD 20 is authorized. Electronic prescription indicator 64 may correspond with more than two designated bits in which case electronic prescription indicator 64 may be set for more than four values.

User interface 72 may include an output mechanism to provide an indication to the user to confirm that IMD 20 is authorized for a medical procedure and, in some instances, the type of medical procedure for which IMD 20 is authorized. As described in further detail below, the output mechanism of user interface 72 may include a display, one or more visual indicators, or one or more audible indicators to provide the indication to the user confirming that is authorized for the medical procedure.

Upon determining that IMD 20 is programmed with an electronic prescription 66 based on electronic prescription indicator 64, processor 74 may generate another telemetry communication and transmits the communication to IMD 20 to invoke device operating parameters defined by electronic prescription 66, e.g., the exposure operating mode designed for operation in disruptive energy field 18. In one example, user interface 72 may include a button that the user actuates to initiate configuration of IMD 20 into the exposure operating mode. The button may be the same as the interrogation button or a different button. In response to receiving the communication, IMD 20 may write to an operating mode register of IMD 20 to the cause of IMD 20 to be configured into the exposure operating mode.

Telemetry device 16 may receive another communication from IMD 20 that confirms that IMD 20 is operating in accordance with the exposure operating mode. User interface 72 of telemetry device 16 may provide an indication to the user that IMD 20 is now operating in the exposure operating mode. User interface 72 may provide the indication via the display, one or more visual indicators, or one or more audible indicators. In one example, user interface 72 may include one or more light emitting diodes (LEDs) that may be lit with different colors based on whether electronic prescription indicator 64 is set and whether IMD 20 is operating in accordance with the exposure operating mode. For instance, LED may be red when electronic prescription indicator 64 is not set, a yellow when electronic prescription indicator 64 is set but IMD 20 is not operating in the exposure operating mode, a green when IMD 20 is operating in the exposure operating mode. In this case, the medical procedure will not proceed until the LED is green.

Power source 78 of telemetry device 16 delivers operating power to the components of telemetry device 16. Power source 78 may include a rechargeable or non-rechargeable battery. In other embodiments, telemetry device 16 may be directly coupled to an alternating current (AC) outlet to power telemetry device 16.

Processor 74 may control operation of telemetry device 16, e.g., by controlling operation of the various components of telemetry device 16. Memory 76 may include computer-readable instructions that, when executed by processor 74, cause telemetry device 16 to perform various functions attributed to the components of telemetry device 16 herein. Processor 74 may include one or more of a microprocessor, a controller, a DSP, an ASIC, an FPGA, or equivalent discrete or integrated logic circuitry. In some examples, processor 74 may include multiple components, such as any combination of one or more microprocessors, one or more controllers, one or more DSPs, one or more ASICs, or one or more FPGAs, as well as other discrete or integrated logic circuitry. The functions attributed to processor 74 herein may be embodied as software, firmware, hardware or any combination thereof. Memory 76 may include any volatile, non-volatile, magnetic, optical, or electrical media, such as a RAM, ROM, NVRAM, SRAM, EEPROM, flash memory, or any other computer-readable storage media or a combination thereof.

Telemetry module 70 of telemetry device 16 communicates wirelessly with telemetry module 54 of IMD 20 by any of a number of communication protocols designed for communication with IMD 20 and/or wireless communication techniques described in detail above with respect to telemetry module 54. As such, telemetry module 70 may include appropriate modulation, demodulation, frequency conversion, filtering, and amplifier components for transmission and/or reception of data.

Figure 5:
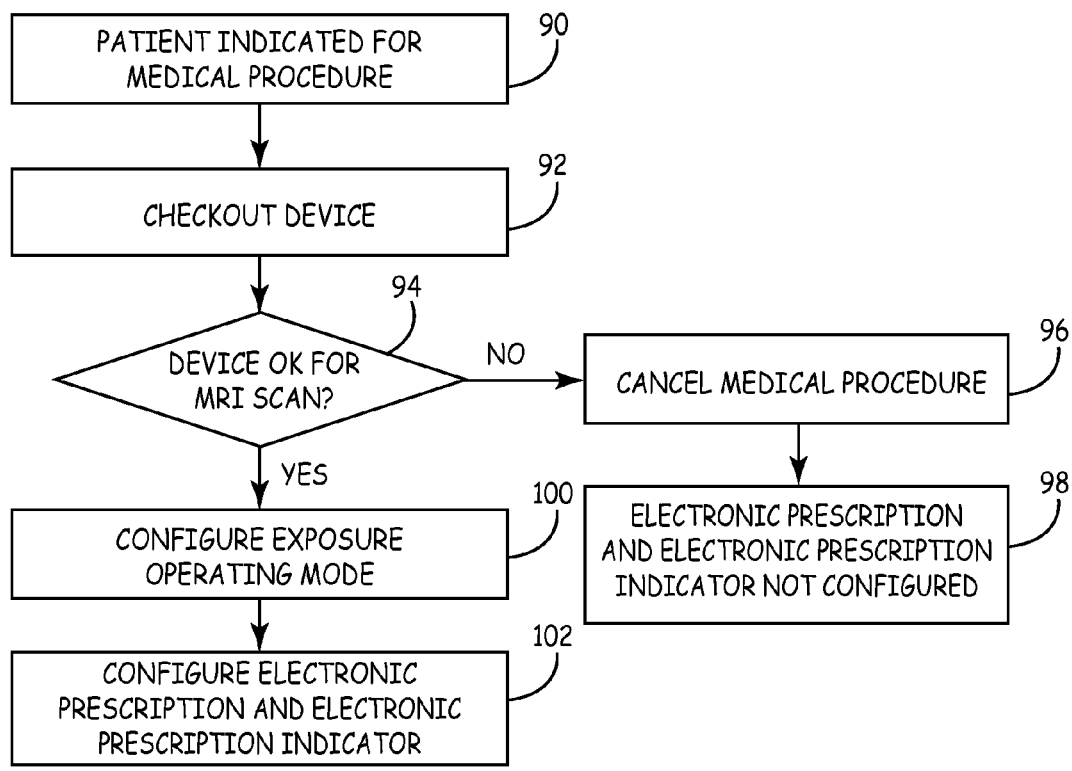
FIG. 5 is a flow diagram illustrating an example operation of a telemetry device configuring an electronic prescription of an IMD.

FIG. 5 is a flow diagram illustrating example operation of a telemetry device (such as telemetry device 17) configuring an electronic prescription of an IMD 20. Initially, patient 12 is indicated for a medical procedure (90). Patient 12 may, for example, be indicated for an MRI scan or other medical procedure.

Prior to having the medical procedure, IMD 20 is checked out to determine suitability for operation in disruptive energy field 18 (92). In one example, a person may determine whether IMD 20 is MRI labeled by looking for a radio opaque mark on IMD 20 in an x-ray of a chest of patient 12. In another example, a user may interact with a telemetry device (e.g., telemetry device 17) to determine a product serial number, model number, model type or other identifier of IMD 20 and use the identifier to determine whether IMD 20 is MRI labeled. In a further example, the user may interact with telemetry device 17 to cause IMD 20 to perform one or more tests to determine whether IMD 20 is suitable for operation in disruptive energy field 18. Upon determining that IMD 20 is not suitable for operation in disruptive energy field 18 ("NO" branch of block 94), the medical procedure is canceled (96) and electronic prescription indicator 64 is not configured (98).

Upon determining that IMD 20 is suitable for operation in disruptive energy field 18 ("YES" branch of block 94), telemetry device 17 may transmit one or more communications to configure electronic prescription 66, e.g., operating parameters for the exposure operating mode (100). For example, the one or more communications may specify a pacing mode (e.g., atrial-based pacing mode, ventricular-based pacing mode or dual-chamber based pacing mode), pacing amplitude, pacing pulse width, and/or pacing rate of the therapy energy delivered during the exposure operating mode. As another example, the user may specify filtering configurations to be used during the exposure operating mode. In other instances, IMD 20 may include preconfigured operating parameters for the exposure operating mode or automatically determine the exposure operating mode. In this case, step 100 may be viewed as an optional step in some instances.

In addition, telemetry device 17 may transmit on a more communications to configure electronic prescription 66 and electronic prescription indicator 64 (102). Telemetry device 17 may, for example, transmit one or more communications that cause IMD 20 to assert or set the one or more designated bits that make up electronic prescription indicator 64. In this manner, telemetry device 17 may configure electronic prescription indicator 64 to indicate that IMD 20 is authorized for the MRI scan or other medical procedure that includes disruptive energy field 18.

As described above, it may be desirable in some instances for processor 56 of IMD 20 to continually and automatically update electronic prescription 66 and/or electronic prescription indicator 64 between when electronic prescription 66 is configured and when patient 12 arrives for the medical procedure. Upon making such an adjustment, IMD 20 may notify patient 12 and/or a physician regarding such a change.

Figure 6:
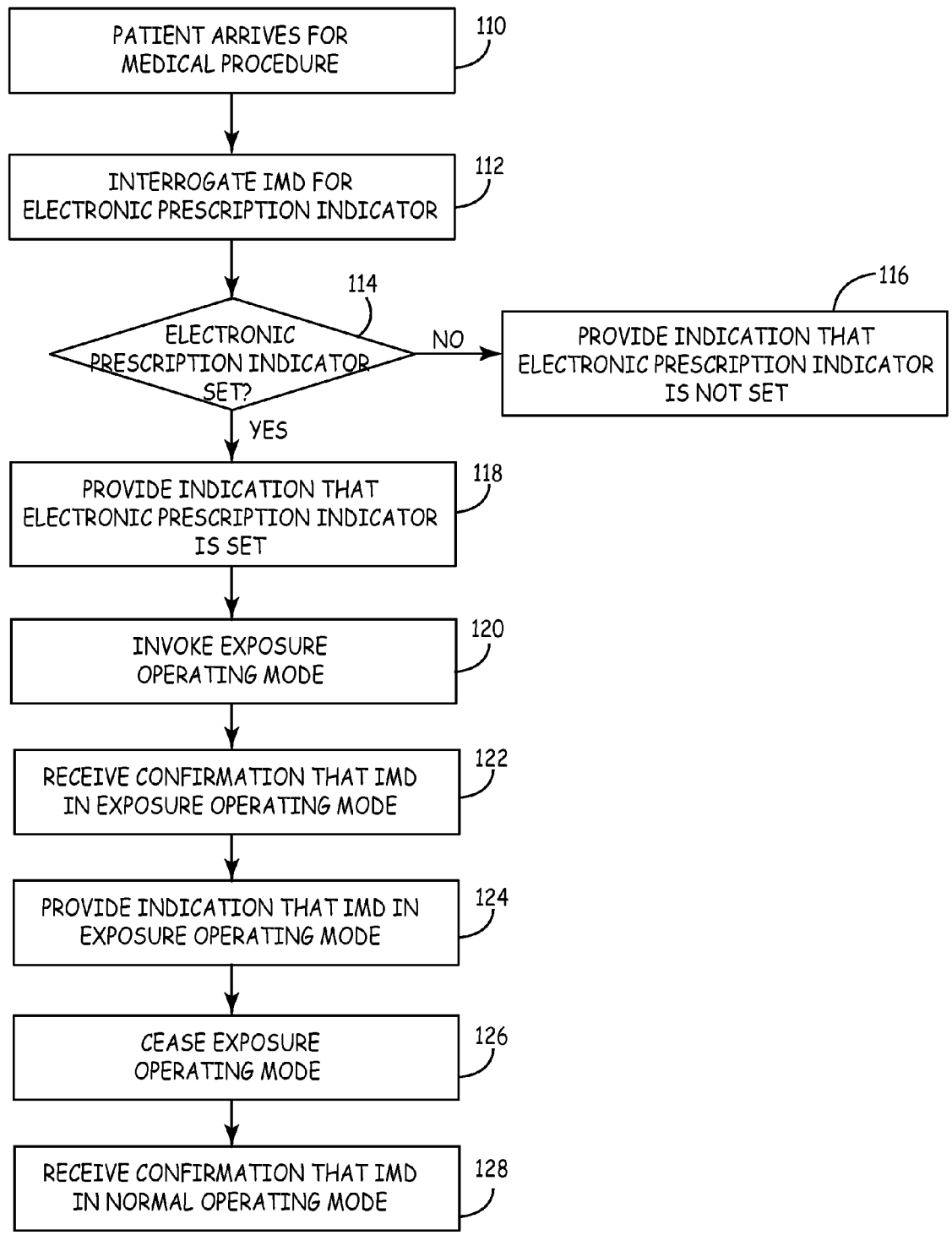
FIG. 6 is a flow diagram illustrating an example operation of a telemetry device invoking an exposure operating mode of an IMD upon confirming that an electronic prescription is set in the IMD.

FIG. 6 is a flow diagram illustrating example operation of a telemetry device (such as telemetry device 16) invoking an electronic prescription of IMD 20 upon confirming that electronic prescription indicator 64 is set. Initially, a patient arrives for a medical procedure (110). Telemetry device 16 generates and sends one or more telemetry communications to interrogate IMD 20 regarding electronic prescription indicator 64 (112). In one example, user interface 72 may include an interrogation button that the user actuates to initiate interrogation of IMD 20.

Telemetry device 16 may receive a telemetry communication from IMD 20 indicating whether electronic prescription indicator 64 of IMD 20 is set (114). The telemetry communication from IMD 20 may indicate a value of electronic prescription indicator 64 and processor 74 of telemetry device 16 may determine whether electronic prescription indicator 64 is set based on the indicated value of electronic prescription indicator 64. In the example in which electronic prescription indicator 64 is one designated bit, processor 74 may determine that electronic prescription indicator 64 is set when equal to "1" and determined that electronic prescription indicator 64 is not set when equal to "b 0."

When electronic prescription indicator 64 is not set ("NO" branch of block 114), user interface 72 indicates to the user that electronic prescription indicator 64 is not set (116). For example, user interface 72 of telemetry device 16 may indicate to the user that electronic prescription indicator 64 is not set using an LED, a display, or other output mechanism. In instances where electronic prescription indicator 64 is not set, the medical procedure may be canceled.

When electronic prescription indicator 64 is set ("YES" branch of block 114), user interface 72 may indicate to the user that electronic prescription indicator 64 is set (118). For example user interface 72 of telemetry device 16 may indicate to the user that electronic prescription indicator 64 is set by lighting the LED in a different color, such as yellow instead of red. Furthermore, processor 74 may generate another telemetry communication and transmits the communication to IMD 20 to invoke the exposure operating mode (120). In one example, processor 74 may automatically generate and transmit the telemetry communication upon determining that electronic prescription indicator 64 is configured. In another example, processor 74 may generate and transmit the telemetry communication in response to an input from the user, such as in response to actuation of a button of the user interface 72 of telemetry device 16.

Telemetry device 16 may receive another communication from IMD 20 that confirms that IMD 20 is operating in accordance with the exposure operating mode or the programmed electronic prescription (122). User interface 72 of telemetry device 16 may provide an indication to the user that IMD 20 is now operating in the exposure operating mode or in accordance with electronic prescription 66 (124). User interface 72 may provide the indication via the display, one or more visual indicators, or one or more audible indicators. In one example, user interface 72 generates the indication by lighting the LED in the third color, such as green instead of yellow or red.

After the medical procedure has been performed, the user may interact with telemetry device 16 to transmit another communication to IMD 20 to cease operation of IMD 20 in the exposure operating mode (126). Telemetry device 16 may receive a communication from IMD 20 that confirms that IMD 20 is operating in accordance with the normal operating mode (128).

Figure 7:
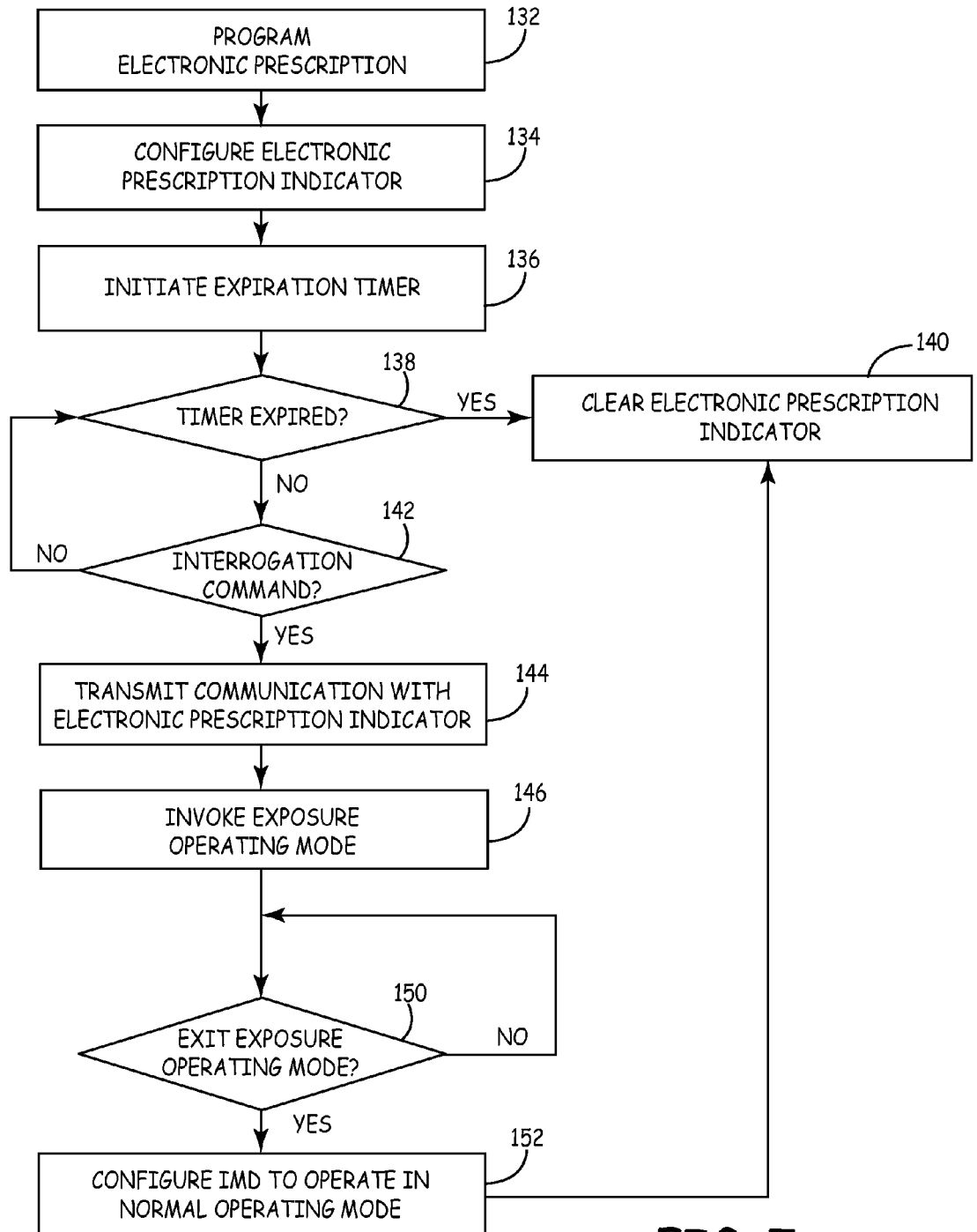
FIG. 7 is a flow diagram illustrating an example operation of an IMD in accordance with the techniques of this disclosure.

FIG. 7 is a flow diagram illustrating example operation of IMD 20 in accordance with the techniques of this disclosure. Prior to having a medical procedure for which patient 12 has been indicated, such as an MRI scan, IMD 20 is programmed with electronic prescription 66 (132). IMD 20 may, for example, receive one or more communications from telemetry device 17 to program the electronic prescription, e.g., by programming one or more device operating parameters. In other instances, IMD 20 may be preconfigured with electronic prescription 66 or automatically determine electronic prescription 66.

IMD 20 also configures electronic prescription indicator 64 to indicate that IMD 20 is authorized for the MRI scan or other medical procedure (134). IMD 20 may configure electronic prescription indicator 64 in response to the communication from telemetry device 17. Alternatively, processor 56 of IMD 20 may automatically configure electronic prescription indicator 64 after electronic prescription 66 is programmed Processor 56 may initiate an expiration timer to track the amount of time that has elapsed since electronic prescription 66 or electronic prescription indicator 64 was configured (136). Processor 56 may monitor the expiration timer to determine whether the expiration timer is expired (138). When the expiration timer is expired ("YES" branch of block 138), processor 56 clears electronic prescription indicator 64 (e.g., reset, deassert or reconfigure electronic prescription indicator 64 to a default value) (140).

If the expiration timer is not expired ("NO" branch of block 138), processor 56 monitors for an interrogation command from a second telemetry device, e.g., telemetry device 16 (142). When no interrogation command is received from the second telemetry device ("NO" branch of block 142), processor 56 determines whether the expiration timer is expired as described above with respect to block 138. When interrogation command is received from telemetry device 16, ("YES" branch of block 142), IMD 20 transmits a communication that indicates whether electronic prescription indicator 64 is configured (144). IMD 20 may, for example, transmit a communication to telemetry device 16 with the value of electronic prescription indicator 64 or an indication as to whether electronic prescription indicator 64 has been configured.

Processor 56 of IMD 20 invokes electronic prescription 66, e.g., transition into the exposure operating mode (146). For example, processor 56 may invoke electronic prescription 66 in response to receiving a second command from telemetry device 16 to invoke electronic prescription 66. In response to the second command, processor 56 begins to operate IMD 20 in accordance with the operating parameters of the exposure operating mode defined by electronic prescription 66 (148). Upon entering the exposure operating mode, IMD 20 may transmit a communication to telemetry device 16 to indicate that IMD 20 is now operating in accordance with the exposure operating mode. In this manner, confirmation that IMD 20 is operating in the exposure operating mode defined by electronic prescription 66 may be obtained before performing the MRI scan or other medical procedure.

Processor 56 determines whether to exit the exposure operating mode (150). In one example, processor 56 may receive a telemetry communication from telemetry device 16 that indicates to processor 56 that it may now exit the exposure operating mode. In another example, processor 56 of IMD 20 may determine whether to exit the exposure operating mode based on a condition or a combination of conditions, such as expiration of a timer, disruptive field detector 62 no longer detecting disruptive energy field 18 or the like. When processor 56 determines to not exit the exposure operating mode ("NO" branch of block 150), processor 56 continues to operate IMD 20 in accordance with the exposure operating mode (148). When processor 56 determines to exit the exposure operating mode ("YES" branch of block 150), processor 56 transitions to the normal operating mode (152) and clears electronic prescription indicator 64 as described with respect to block 140.

As described above, if electronic prescription indicator 64 is not configured or IMD 20 is not interrogated prior to exposure to disruptive energy field 18, IMD 20 may still enter an exposure operating mode upon exposure to disruptive energy field 18. For example, processor 56 may configure IMD 20 into a default exposure operating mode (when electronic prescription indicator 64 is not configured) or into the configured electronic prescription mode (when electronic prescription indicator 64 is configured) in response to disruptive field detector 62 detecting the existence of an environment have a potentially disruptive energy field.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method of configuring an implantable medical device for operation in an environment with a disruptive energy field, the method comprising:
configuring an electronic prescription indicator to indicate whether the implantable medical device is authorized for a medical procedure that includes the disruptive energy field, wherein the electronic prescription indicator includes one or more designated bits within a storage element of the implantable medical device;
confirming that the electronic prescription indicator of the implantable medical device is configured;
invoking an exposure operating mode defined by an electronic prescription that is designed for operation in the disruptive energy field upon confirming that the electronic prescription indicator is configured; and
initiating a timer in response to configuring the electronic prescription indicator, wherein the timer tracks the amount of time that has elapsed since configuring the electronic prescription indicator; and
clearing the electronic prescription indicator upon expiration of the timer.

2. The method of claim 1,
further comprising determining whether the implantable medical device is suitable for operation in the disruptive energy field,
wherein configuring the electronic prescription indicator comprises configuring the electronic prescription indicator when the implantable medical device is determined to be suitable for operation in the disruptive energy field.

3. The method of claim 1, further comprising defining operating parameters to be used when operating in the exposure operating mode.

4. The method of claim 3, further comprising automatically updating at least one of the operating parameters after defining the operating parameters and prior to exposure to the disruptive energy field.

5. The method of claim 1, wherein invoking the exposure operating mode comprises writing to at least one register of the implantable medical device upon confirming that the electronic prescription indicator is configured to cause the implantable medical device to operate in the exposure operating mode defined by the electronic prescription.

6. The method of claim 1, further comprising:
transitioning from the exposure operating mode to a normal operating mode after the medical procedure; and
clearing the electronic prescription indicator after the medical procedure.

7. The method of claim 1, wherein the electronic prescription indicator includes a plurality of designated bits and configuring the electronic prescription indicator comprises configuring the electronic prescription indicator to indicate a type of medical procedure for which the implantable medical device is authorized.

8. The method of claim 7, wherein configuring the electronic prescription indicator to indicate the type of medical procedure comprises:
configuring the electronic prescription indicator to a first value to indicate that the implantable medical device is authorized for a first type of medical procedure; and
configuring the electronic prescription indicator to a second value to indicate that the implantable medical device is authorized for a second type of medical procedure.

9. The method of claim 1, wherein the electronic prescription indicator includes one designated bit and configuring the electronic prescription indicator comprises asserting the one designated bit.

10. The method of claim 1, further comprising:
providing a first indication to a user to confirm that the electronic prescription indicator of the implantable medical device is configured; and
providing a second indication to the user to confirm that the implantable medical device is operating in the exposure operating mode.

11. A medical device system comprising:
an implantable medical device that includes:
a telemetry module to transmit and receive communications;
an electronic prescription indicator that indicates whether the implantable medical device is authorized for a medical procedure that includes a disruptive energy field, wherein the electronic prescription indicator includes one or more designated bits within a storage element of the implantable medical device;
an electronic prescription that defines operating parameters of an exposure operating mode that is designed for operation in the disruptive energy field; and
a processor, wherein the processor of the implantable medical device initiates a timer to track the amount of time that has elapsed since the electronic prescription indicator was configured and clears the electronic prescription indicator upon expiration of the timer;
a first external device that communicates with the implantable medical device to cause the processor to configure the electronic prescription indicator to indicate that the implantable medical device is authorized for a medical procedure that includes a disruptive energy field; and
a second external device that communicates with the implantable medical device to confirm that the electronic prescription indicator of the implantable medical device is configured and invoke the electronic prescription upon confirming that the electronic prescription indicator is configured.

12. The system of claim 11, wherein the first external device determines whether the implantable medical device is suitable for operation in the disruptive energy field and communicates with the implantable medical device to cause the processor to configure the electronic prescription indicator when the implantable medical device is determined to be suitable for operation in the disruptive energy field.

13. The system of claim 11, wherein the first external device communicates with the implantable medical device to cause the processor to program at least a portion of the operating parameters to be used when operating in the exposure operating mode.

14. The system of claim 11, wherein the second external device communicates with the implantable medical device to cause the processor to write to at least one register of the implantable medical device upon confirming that the electronic prescription indicator is configured to cause the implantable medical device to operate in an exposure operating mode defined by the electronic prescription.

15. The system of claim 11, wherein the processor of the implantable medical device transitions operation of the implantable medical device from the exposure operating mode to a normal operating mode after the medical procedure and clears the electronic prescription indicator after the medical procedure.

16. The system of claim 11, wherein the electronic prescription indicator includes a plurality of designated bits and the processor configures the electronic prescription indicator to indicate a type of medical procedure for which the implantable medical device is authorized.

17. The system of claim 16, wherein processor configures the electronic prescription indicator to a first value to indicate that the implantable medical device is authorized for a first type of medical procedure and configures the electronic prescription indicator to a second value to indicate that the implantable medical device is authorized for a second type of medical procedure.

18. The system of claim 11, wherein the electronic prescription indicator includes one designated bit and the processor configures the electronic prescription by asserting the one designated bit.

19. The system of claim 11, wherein the second external device provides a first indication to a user to confirm that the electronic prescription indicator of the implantable medical device is configured and provides a second indication to the user to confirm that the implantable medical device is operating in the exposure operating mode defined by the electronic prescription.

20. An implantable medical device comprising:
at least one storage element;
an electronic prescription indicator that indicates whether the implantable medical device is authorized for a medical procedure that includes a disruptive energy field, wherein the electronic prescription indicator includes one or more designated bits within the at least one storage element of the implantable medical device;
an electronic prescription that defines one or more device operating parameters of an exposure operating mode for use in the disruptive energy field, wherein the electronic prescription is stored within the at least one storage element of the implantable medical device;
a transceiver that transmits and receives communications; and
a processor that controls operation of the implantable medical device, wherein the processor configures the electronic prescription indicator to indicate that the implantable medical device is configured with the electronic prescription and causes the transceiver to transmit a communication that includes a value of the electronic prescription indicator in response to a communication from an external device, wherein the processor initiates a timer in response to configuring the electronic prescription indicator to track the amount of time that has elapsed since configuring the electronic prescription indicator and clears the electronic prescription indicator upon expiration of the timer.

21. The implantable medical device of claim 20, wherein the processor configures the electronic prescription indicator in response to a communication from a second external device.

22. The implantable medical device of claim 20, wherein the processor automatically configures the electronic prescription indicator when the electronic prescription is manually configured.

23. The implantable medical device of claim 20, wherein the electronic prescription is one designated bit within the at least one storage element and the processor sets the electronic prescription indicator to "1" when the implantable medical device is configured with the electronic prescription and sets the electronic prescription indicator to "0" when the implantable medical device is not configured with the electronic prescription.

24. The implantable medical device of claim 20, wherein the electronic prescription indicator includes a plurality of bits and the processor configures the electronic prescription indicator to indicate a type of procedure from a plurality of possible procedures for which the electronic prescription is configured.

25. The implantable medical device of claim 20, wherein the processor automatically updates the electronic prescription after the electronic prescription is configured and before the device is exposed to the disruptive energy field.

26. The implantable medical device of claim 20, wherein the processor automatically updates the electronic prescription indicator after the electronic prescription indicator is configured and before the device is exposed to the disruptive energy field.

27. The implantable medical device of claim 20, wherein the processor begins to operate the implantable medical device in accordance with the device operating parameters defined by the electronic prescription in response to a second communication received from the external device.

28. The implantable medical device of claim 27, wherein the processor causes the transceiver to transmit a third communication to indicate that the implantable medical device is operating in accordance with the device operating parameters defined by the electronic prescription.

29. The implantable medical device of claim 20, wherein the processor begins to operate the implantable medical device in accordance with the device operating parameters defined by the electronic prescription in response to the first communication from the external device.

* * * * *

UNITED STATES PATENT AND TRADEMARK OFFICE
CERTIFICATE OF CORRECTION

PATENT NO.        : 8,838,254 B2                                    Page 1 of 1
APPLICATION NO.   : 12/872352
DATED             : September 16, 2014
INVENTOR(S)       : Lawrence C. McClure et al.

It is certified that error appears in the above-identified patent and that said Letters Patent is hereby corrected as shown below:

In the Claims

Claim 17, Column 24, lines 16-18, delete "... The system of claim 16, wherein processor configures the electronic prescription indicator to a first value to indicate that the implantable ..." and insert in place thereof -- ... The system of claim 16, wherein the processor configures the electronic prescription indicator to a first value to indicate that the implantable ... --

Signed and Sealed this
Fourth Day of August, 2015

Michelle K. Lee
*Director of the United States Patent and Trademark Office*